(12) United States Patent
Fleury et al.

(10) Patent No.: US 9,021,867 B2
(45) Date of Patent: May 5, 2015

(54) SENSOR-ENABLED GATE VALVE

(71) Applicant: Mueller International, LLC, Atlanta, GA (US)

(72) Inventors: Leo W. Fleury, N. Smithfield, RI (US); Normand James Roy, Coventry, RI (US); James Ola Williams, Marlborough, MA (US); Kenneth A. Clark, Chattanooga, TN (US)

(73) Assignee: Mueller International, LLC, Atlanta, GA (US)

( * ) Notice: Subject to any disclaimer, the term of this patent is extended or adjusted under 35 U.S.C. 154(b) by 107 days.

(21) Appl. No.: 13/753,428

(22) Filed: Jan. 29, 2013

(65) Prior Publication Data

US 2013/0192348 A1  Aug. 1, 2013

Related U.S. Application Data

(60) Provisional application No. 61/592,321, filed on Jan. 30, 2012.

(51) Int. Cl.
| | | |
|---|---|---|
| *F16K 3/00* | (2006.01) | |
| *G01N 33/18* | (2006.01) | |
| *F16K 37/00* | (2006.01) | |
| *F16K 3/02* | (2006.01) | |
| *F16K 27/04* | (2006.01) | |

(52) U.S. Cl.
CPC ....... *F16K 3/00* (2013.01); *G01N 33/18* (2013.01); *F16K 37/00* (2013.01); *F16K 3/0209* (2013.01); *F16K 27/044* (2013.01)

(58) Field of Classification Search
USPC .............. 73/53.01, 64.56, 863.86; 137/551; 251/326
See application file for complete search history.

(56) References Cited

U.S. PATENT DOCUMENTS

| | | | |
|---|---|---|---|
| 4,696,325 A | 9/1987 | Magee | |
| 4,968,002 A | 11/1990 | Gibson et al. | |
| 5,056,758 A | 10/1991 | Bramblet | |
| 5,616,829 A | 4/1997 | Balaschak et al. | |
| 5,728,942 A | 3/1998 | Boger | |
| 6,240,789 B1 | 6/2001 | Morlan et al. | |
| 6,338,359 B1 * | 1/2002 | Welker ........................ | 137/317 |
| 6,698,444 B1 | 3/2004 | Enston | |

FOREIGN PATENT DOCUMENTS

GB         2511014         8/2014

OTHER PUBLICATIONS

Fleury, Leo W.; U.S. Provisional Patent Application entitled: Sensor-Enabled Gate Valve having U.S. Appl. No. 61/592,321, filed Jan. 30, 2012, 27 pgs.

(Continued)

*Primary Examiner* — Daniel S Larkin
(74) *Attorney, Agent, or Firm* — Taylor English Duma LLP

(57) ABSTRACT

Methods, systems, and apparatus for a gate valve including a body and a sensing bore. A subassembly includes a body with a sensing bore; a bonnet contacting the body; and at least one of a vein and a plug in the sensing bore.

13 Claims, 16 Drawing Sheets

(56) References Cited

OTHER PUBLICATIONS

Fleury, Leo W.; PCT Application entitled: Sensor-Enabled Gate Valve having serial No. PCT/US13/23755, filed Jan. 30, 2013, 40 pgs.

Fleury, Leo W.; U.S. Provisional Patent Application entitled: Sensor-Enabled Gate Valve having U.S. Appl. No. 61/643,400, filed May 7, 2012, 31 pgs.

Fleury, Leo W.; U.S. Patent Application entitled: Sensor-Enabled Gate Valve having U.S. Appl. No. 13/753,431, filed Jan. 29, 2013, 31 pgs.

Fleury, Leo W.; International Search Report and Written Opinion for serial No. PCT/US13/23755, filed Jan. 30, 2013, mailed Apr. 5, 2013, 11 pgs.

Fleury, Leo W.; Non-Final Office Action for U.S. Appl. No. 13/753,431, filed Jan. 29, 2013, mailed Oct. 1, 2014, 12 pgs.

Fleury, Leo W.; International Preliminary Report on Patentability for serial No. PCT/US2013/023755, filed Jan. 30, 2013, mailed Aug. 14, 2014, 9 pgs.

\* cited by examiner

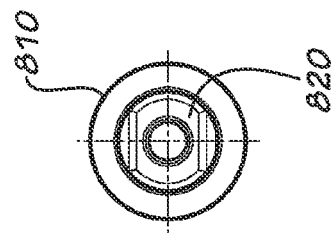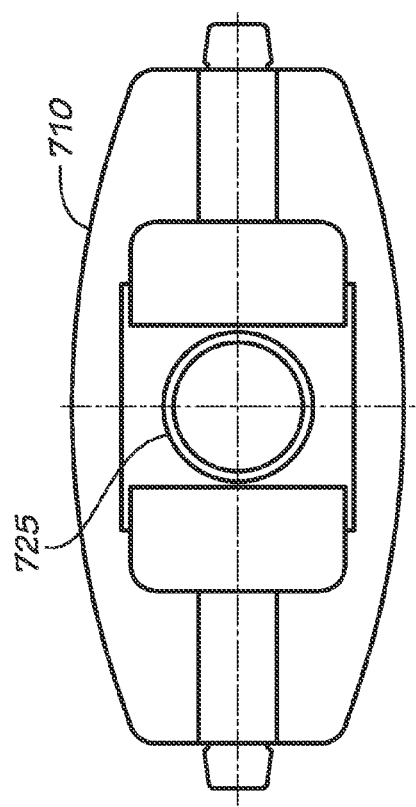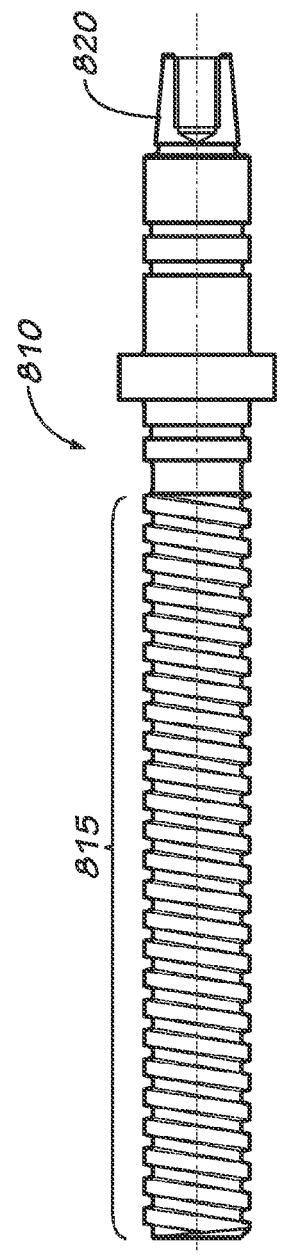

SENSOR-ENABLED GATE VALVE

CROSS-REFERENCE TO RELATED APPLICATIONS

This application claims the benefit of U.S. Provisional Application 61/592,321, filed on Jan. 30, 2012, which is hereby incorporated herein in its entirety by reference.

FIELD

The current disclosure relates to valves. Particularly, the current disclosure relates to gate valves.

BACKGROUND

Valve elements are used to regulate or control the flow of material by opening, closing, or partially obstructing various passageways. One type of valve is a gate valve, which can be used in a number of applications.

SUMMARY

Disclosed is a gate valve having a body, and a sensing bore defined in the gate valve.

Also disclosed is a subassembly including a body, the body defining a sensing bore; a bonnet contacting the body; and at least one of a vein and a plug in the sensing bore.

Also disclosed is a method of sensing an aspect of a water control system, the method including gaining access to the water control system through an access bore in a gate valve; at least temporarily removing water for testing from the access bore; and sensing an aspect of the removed water.

DESCRIPTION OF THE FIGURES

The features and components of the following figures are illustrated to emphasize the general principles of the present disclosure and are not necessarily drawn to scale. Corresponding features and components throughout the figures may be designated by matching reference characters for the sake of consistency and clarity.

FIG. 7C is a top view of the encapsulated disc of FIG. 7A

FIG. 8A is a side view of a stem for use with the subassembly of FIG. 1 in a gate valve.

FIG. 8B is a top view of the stem of FIG. 8A.

DETAILED DESCRIPTION

Figure 1:
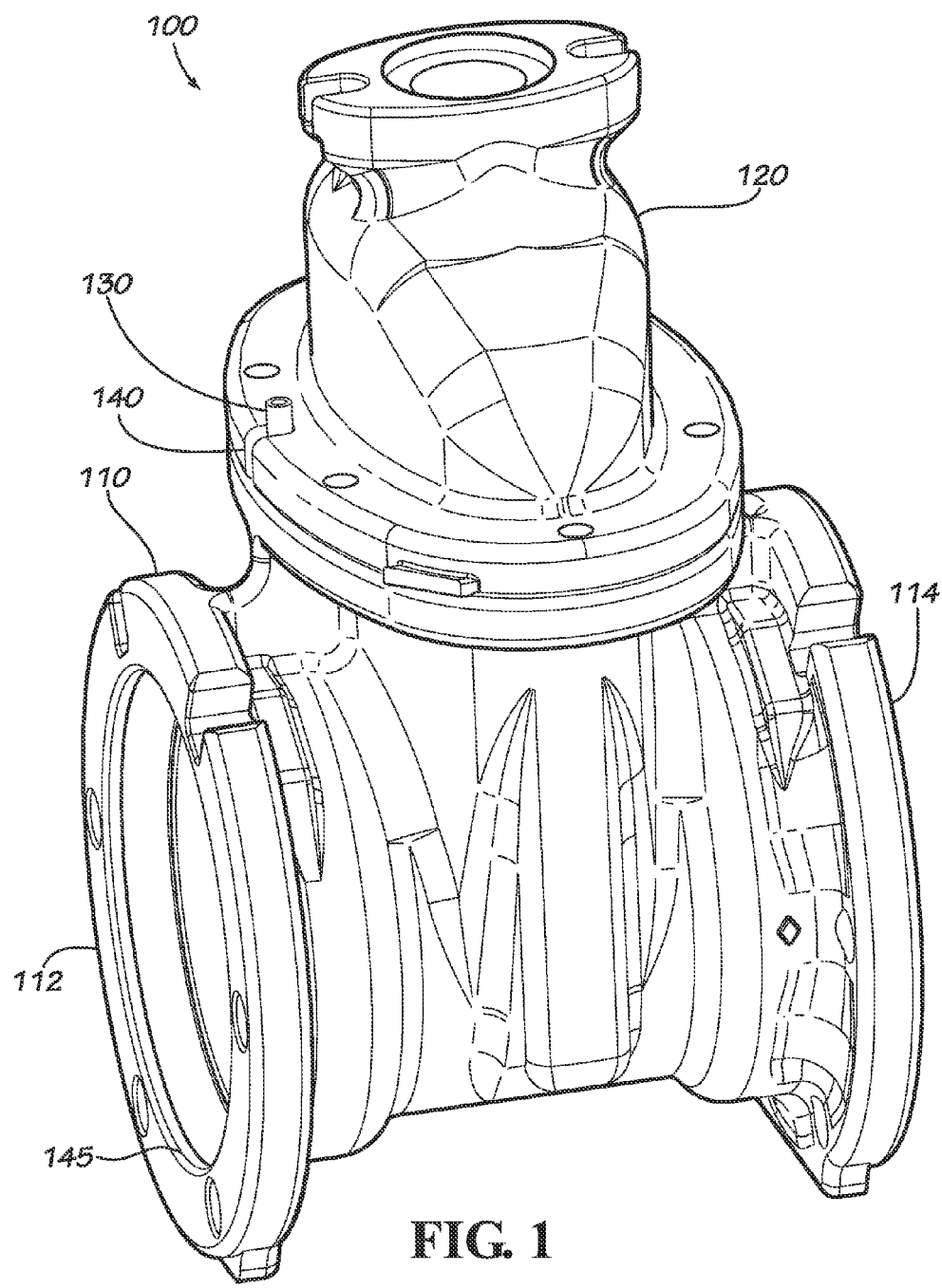
FIG. 1 is a perspective view of a subassembly of a body, a bonnet, and a vein in accord with one embodiment of the current disclosure.

Disclosed are methods, systems, and apparatus associated with sensing characteristics of fluid flow in a gate valve. A subassembly 100 of a body 110, a bonnet 120, and a vein 130 is seen in FIG. 1. The subassembly 100 is incorporated into a gate valve 1000, seen in FIG. 13A. The bonnet 120 includes a notch relief 140 into which the vein 130 fits. The body 110 defines a fluid bore 145 which is substantially continuous from an inlet end 112 to an outlet end 114 of the body 110 to allow fluid flow therein.

Figure 2:
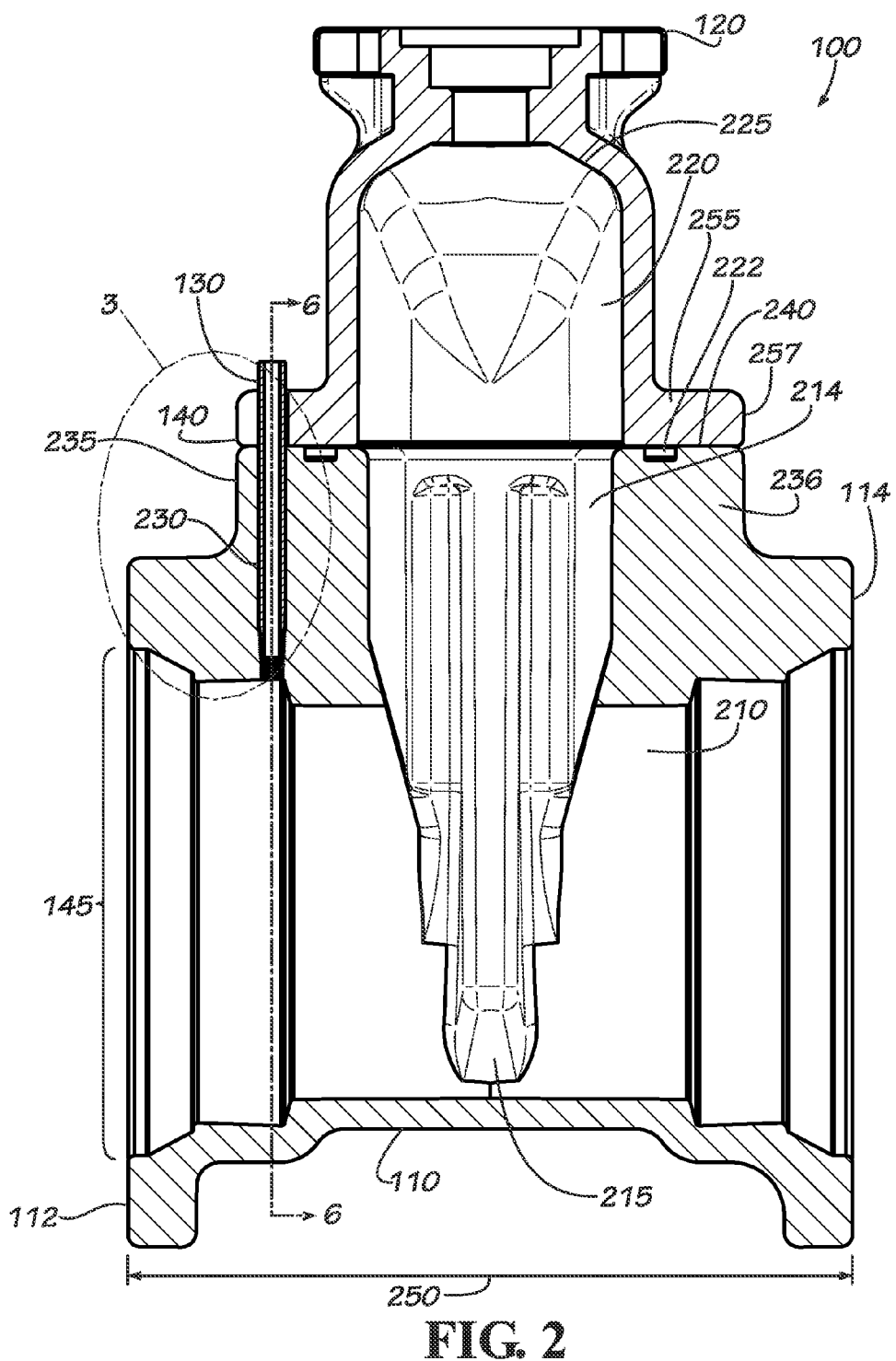
FIG. 2 is a cross-sectional view of the subassembly of FIG. 1.

As seen in cross-sectional view in FIG. 2, an interior 210 of the body 110 is substantially continuous and includes the fluid bore 145 and a valve cavity 214 that is defined within the body 110. The valve cavity 214 includes a valve seat 215. An interior 220 of the bonnet 120 is defined within a cavity 225 of the bonnet 120. The cavity 225 of the bonnet 120 is in fluid communication with the valve seat 215 which is then in fluid communication with the fluid bore 145. In use, fluid flows from the inlet 112 to the outlet 114. The gate valve 1000 incorporating the subassembly 100 includes an encapsulated disc 710 (see FIGS. 7A-7C) as a selective gate to prevent fluid flow. A gasket seat 222 provides space for inclusion of a gasket (not shown) to seal the connection between the bonnet 120 and the body 110. The bonnet 120 includes a flange 255 that matches up with the body 110 over the gasket seat 222, where a flange 655 (seen in FIG. 6) matches that of the flange 255. The flange 255 allows for bolts to secure the bonnet 120 to the body 110. The flange 255 ends at an outermost extent 257. The flange 655 is readily discerned in FIG. 2 because the cross-sectional view is taken through webbing 235. Webbing 236 is seen on the body 110 one opposite side of the valve cavity 214 from webbing 235.

Also seen in FIG. 2, the notch 140 of the bonnet 120 aligns with a sensing bore 230 in the webbing 235 of the body 110. The sensing bore 230 extends from a flange end 240 of the body 110 down to the fluid bore 145. A lay length 250 as measured from the inlet end 112 to the outlet end 114 of the body 110 can also be seen.

Figure 3:
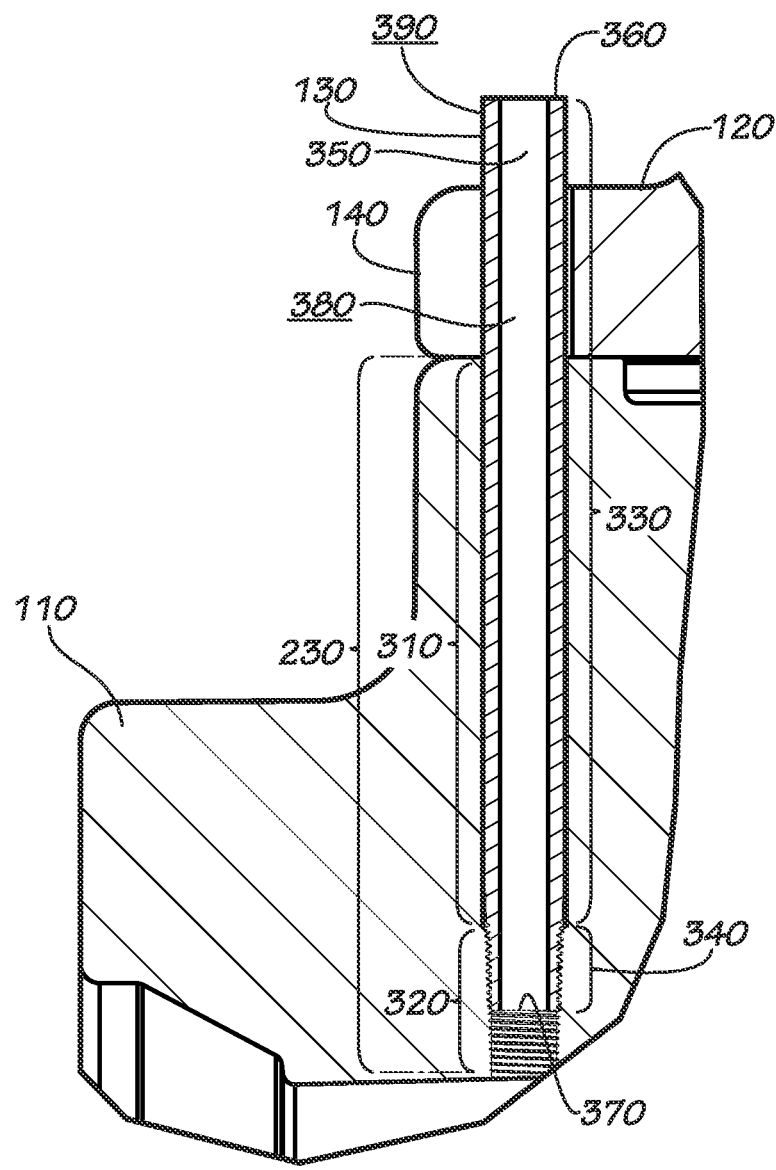
FIG. 3 is a view of the detail denoted by Detail 3 in FIG. 2.

As seen in FIG. 3, the sensing bore 230 includes an insert portion 310 and a threaded portion 320. Likewise, the vein 130 includes a shank portion 330 and a threaded portion 340. As can be seen, the vein 130 defines a bore 350 extending from a shank end 360 of the vein 130 to a thread end 370 of the vein 130 such that the bore 350 is continuous along the entire length of the vein 130. The vein 130 is shown with its threaded portion 340 engaging the threaded portion 320 of the sensing bore 230. This interaction secures the vein 130 in place and seals an interior surface 380 of the vein 130 from an exterior surface 390. Although the vein 130 and the sensing bore 230 are cylindrical in the current embodiment, these shapes should not be considered limiting on the scope of the disclosure.

As seen, the vein 130 extends nearly the entire length of the sensing bore 230. Although some unengaged threads are shown along the threaded portion 320, the vein 130 is designed to extend as far as possible into the sensing bore 230. The vein 130 is made of brass, stainless steel, copper, plastic, or any other type of material subject to low corrosion in an aqueous environment. Typically, the body 110 and the bonnet 120 are made of cast iron, although other similar materials may be used in various embodiments. Because cast iron can be highly corrosive when exposed to water, the extension of the vein 130 into the sensing bore 230 prevents corrosion, pitting, and tuberculation from degrading the ability of fluid to flow through the sensing bore 230. Typically, the body 110 will have a protective coating, but, in some circumstances, such a protective coating may not be applied easily to the interior of the sensing bore 230. However, in some embodiments, no vein 130 will be needed to prevent corrosion because a protective coating may be applied inside the sensing bore 230. In some embodiments, the vein 130 or another vein may be used but may not need to be extended along the entire length of the sensing bore 230.

As seen in FIGS. 1-3, the sensing bore 230 is generally cylindrical although the notch 140 is not. The notch 140 includes a portion that is semi-cylindrical, but the remainder of the notch 140 extends to the outermost extent 257. This configuration of the notch 140 allows for easier assembly of the bonnet 120 onto the body 110 if the vein 130 is already in place. For example, in some embodiments, the vein 130 may be prefabricated with the body 110 or may be preassembled with the body 110 as provided. For another example, in some embodiments, the subassembly 100 may need to be serviced or the bonnet 120 may need to be replaced due to cracking or other failure. Gate valves are designed in sizes ranging from a few inches to several feet in diameter. Particularly in embodiments with larger diameters, the bonnet 120 may be extremely heavy. Some gate valves are as large as 48-inches in diameter, and 24-inch diameter gate valves each include a bonnet weighing approximately 5,000 pounds. As such, attempting to align the vein 130 with a bore in the bonnet 120 may be very difficult. The notch 140 allows a user assembling the subassembly 100 to place the bonnet 120 onto the body 110 and then slide the bonnet 120 into place with the notch 140 aligned to the vein 130 and the sensing bore 230. However, in some embodiments—particularly in embodiments in which the bonnet 120 is relatively light—the bonnet 120 may include a bore instead of the notch 140 with an open side, as in the current embodiment.

One advantage to the placement of the sensing bore 230 and the vein 130 is that the placement does not require an increase in the lay length 250 of the body 110. Thus, the body 110 can be used with piping systems that are already designed for standard lay lengths such as lay length 250. From time to time, such gate valves will need servicing, either to remove blockages in the line, to repair cracked piping, to repair a non-functioning gate valve, or for other purposes. As such, damage to the vein 130 poses a significant risk. Another advantage to the placement of the vein 130 is that it is close to other components of the subassembly 100. As such, the vein 130 may be less-susceptible to movements in the earth whether such movements are seismic or due to assembly, disassembly, and burying of the subassembly 100 in the ground.

Another reason why it is advantageous to place the vein 130 on the subassembly 100 is that the subassembly 100 is part of the gate valve 1000. Pipes in a piping system are typically installed as quickly as possible. Gate valves such as gate valve 1000, on the other hand, are typically handled with care because improper installation of gate valves can lead to leaking piping systems and nonfunctioning gate valves. As such, there is a higher likelihood that sensors such as the pressure sensor—which may be relatively delicate and relatively expensive—are also handled with care if the vein 130 and the pressure sensor are attached to the gate valve 1000 as opposed to another component of the piping system.

Figure 4:
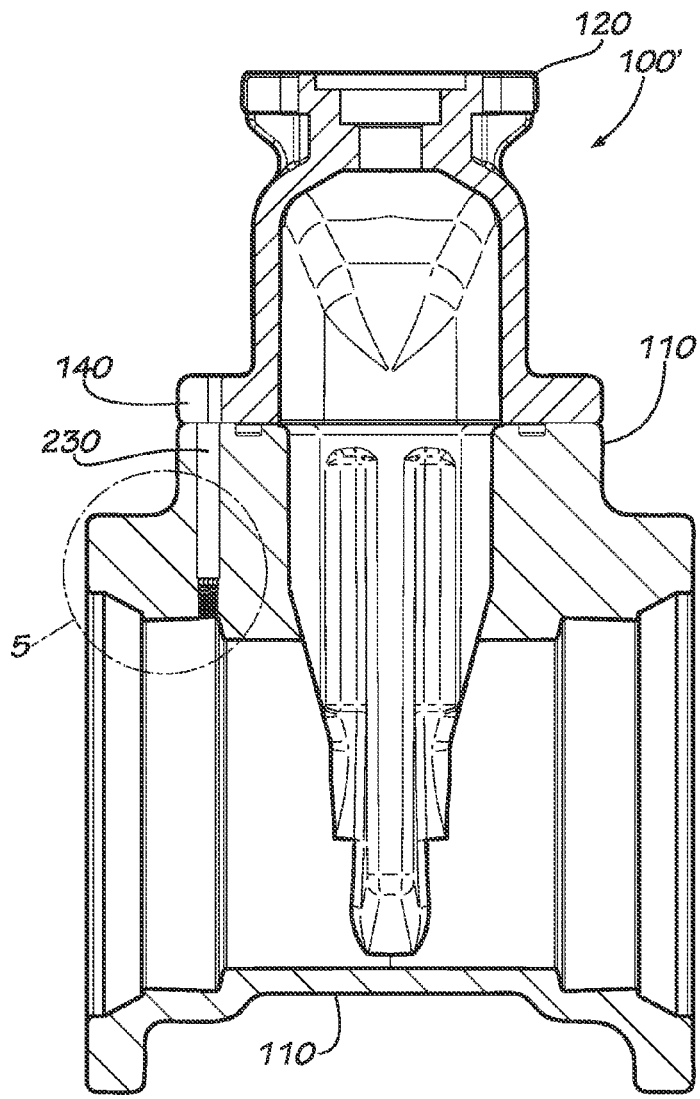
FIG. 4 is a cross-sectional view of a subassembly of the body and the bonnet of FIG. 1 and a plug in accord with one embodiment of the current disclosure.
Figure 5:
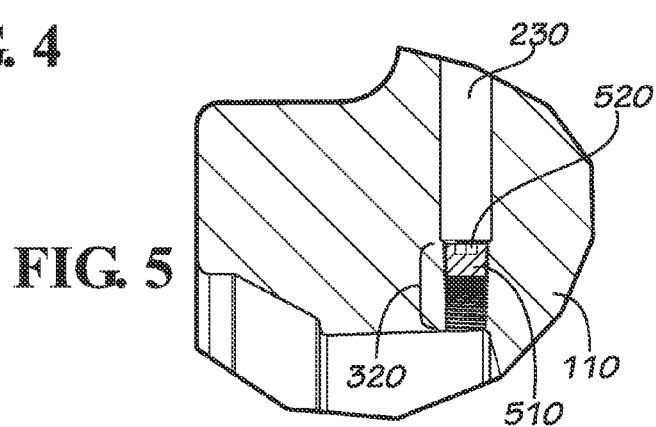
FIG. 5 is a view of the detail denoted by Detail 5 in FIG. 4.

As seen in the embodiments of FIGS. 4 and 5, a subassembly 100' may be substantially the same as subassembly 100. However, in some embodiments, the subassembly 100' may be provided with a plug 510 instead of the vein 130 as in subassembly 100. Such an embodiment as subassembly 100' may make the use of veins 130 optional. In such embodiments, one who assembles the piping system may optionally place the vein 130 or another device into the sensing bore 230 in place of the plug 510. The plug 510 is threaded to engage the threaded portion 320 of the sensing bore 230. As seen, the plug 510 includes a hex head 520 and operates similarly to a set screw in the current embodiment. However, in other embodiments, various configurations of plugs may be used. In some embodiments, a quick-connect adapter may be connected to the sensing bore 230 to allow quick assembly of sensing apparatus. In some embodiments, the vein 130 or a similar probe may be molded in place inside the body 110 casting. In such embodiments, threaded portions 320,340 may be unnecessary as compression from the cooling of the cast iron most likely will retain the vein 130 in place.

Figure 6:
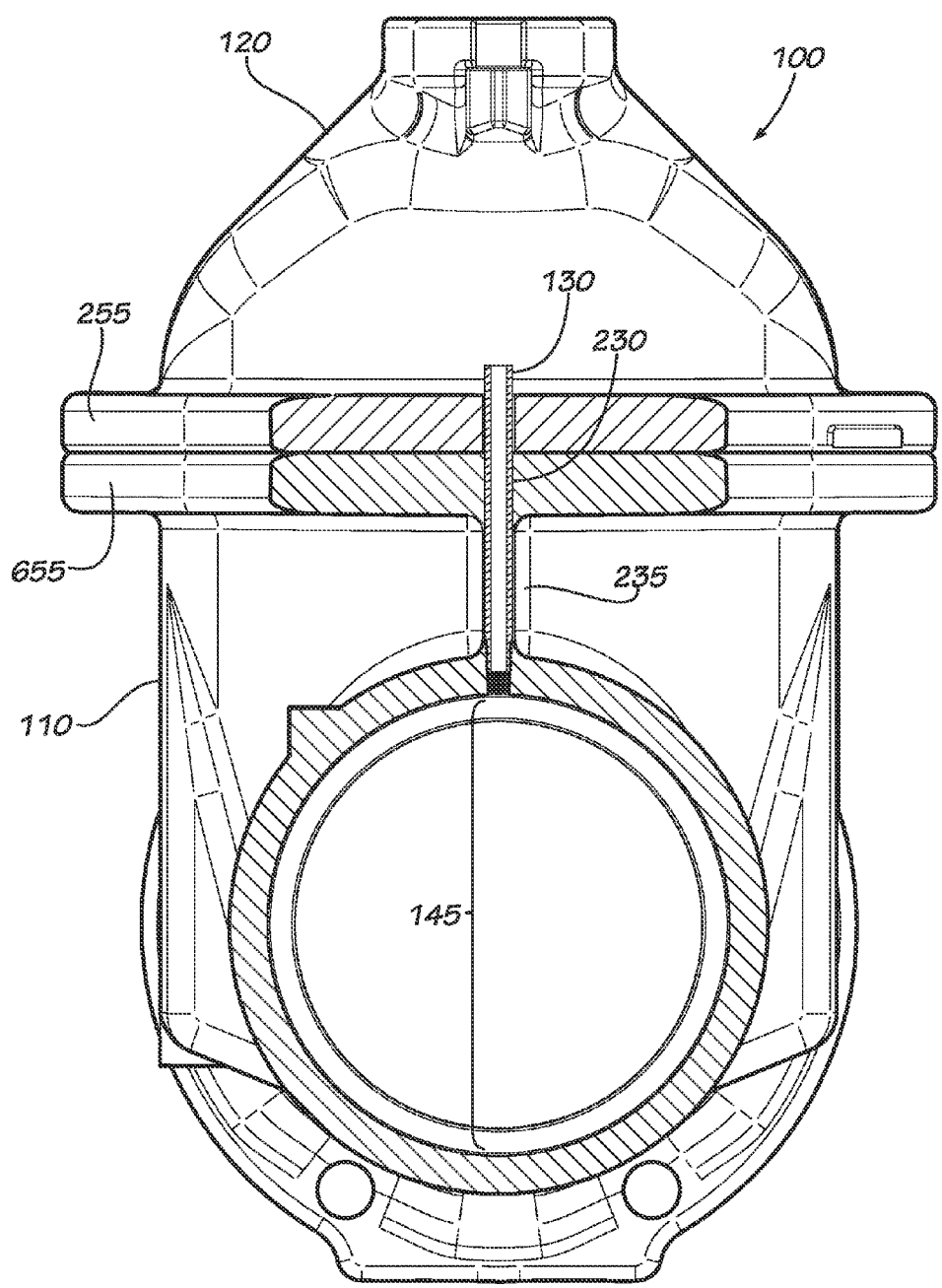
FIG. 6 is a cross-sectional view of the subassembly taken along the plane denoted by line 6 in FIG. 2.

FIG. 6 shows the subassembly 100 on a plane cut through the axis of the vein 130 orthogonal to the cutting plane in the view of FIG. 2. As can be seen, the flange 655 of the body 110 corresponds with the flange 255 of the bonnet 120. The thickness of the webbing 235 can be seen in the view. In various embodiments, the webbing 235 has various thicknesses. As shown, the subassembly 100 includes 6-inch fluid bore 145. The vein 130 is about one-half inch in external diameter. The webbing 235 (and also 236) is about one inch in thickness. As such, the sensing bore 230 is located centrally to retain the structural integrity of the webbing 235. In embodiments of larger size, the webbing 235 may be thicker even if the sensing bore 230 and the vein 130 are not. Thus, in larger size embodiments, placement of the sensing bore 230 is less important. In smaller size embodiments, a smaller vein 130 and sensing bore 230 may be used to accommodate thinner webbing 235.

Figure 7A:
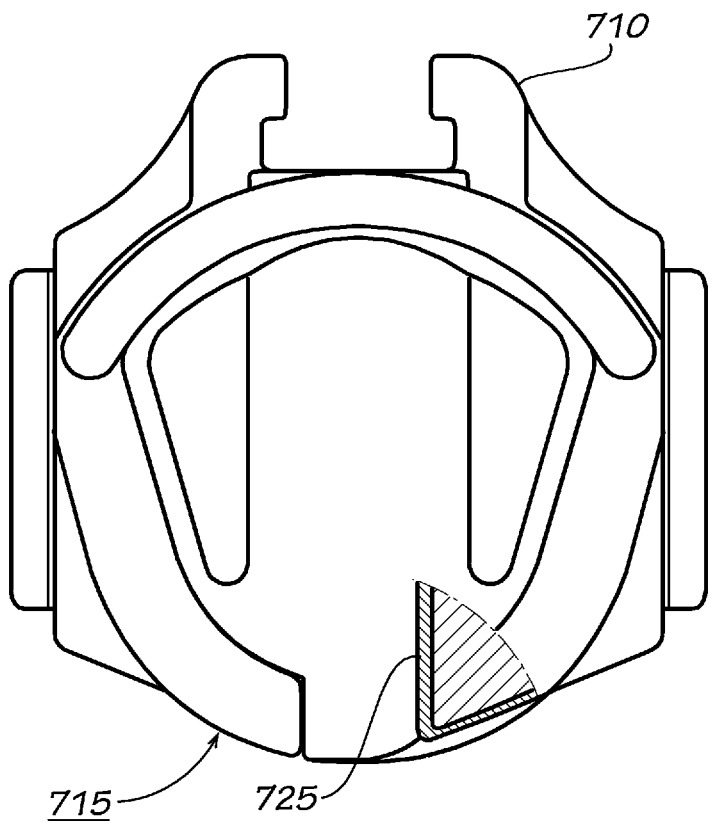
FIG. 7A is a front and partial cross-sectional view of an encapsulated disc for use with the subassembly of FIG. 1 in a gate valve.
Figure 7B:
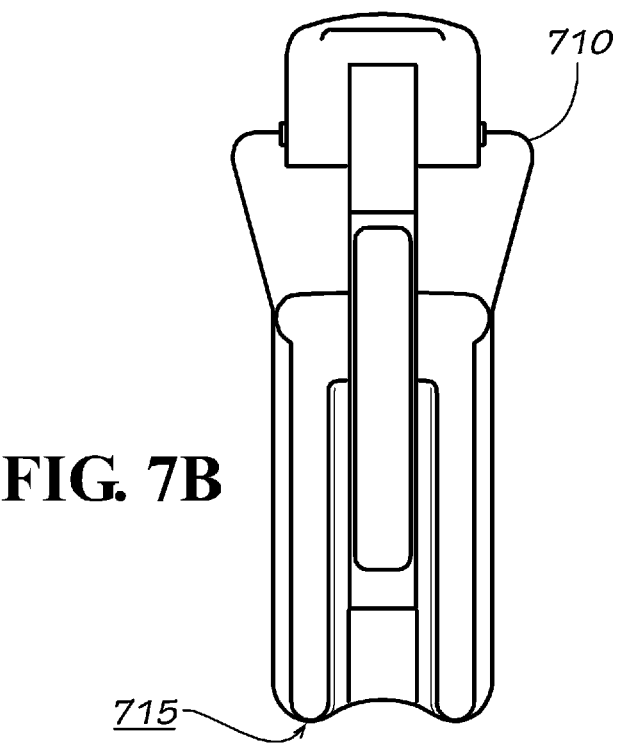
FIG. 7B is a side view of the encapsulated disc of FIG. 7A
Figure 9A:
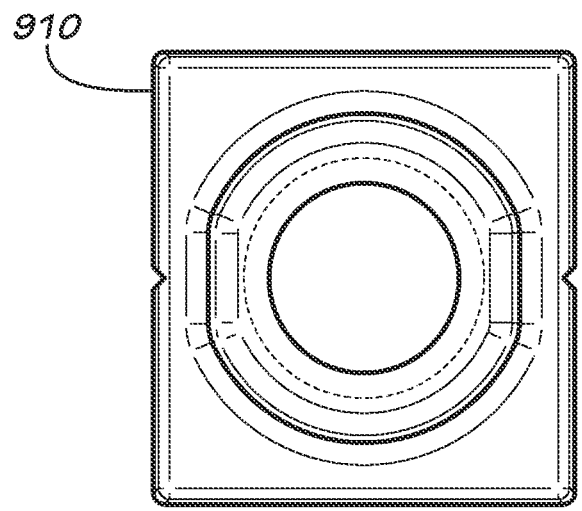
FIG. 9A is a top view of a disc nut for use with the subassembly of FIG. 1 in a gate valve.
Figure 9B:
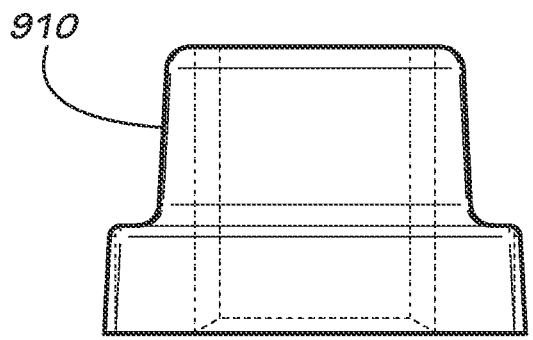
FIG. 9B is a front view of the disc nut of FIG. 9A.
Figure 9C:
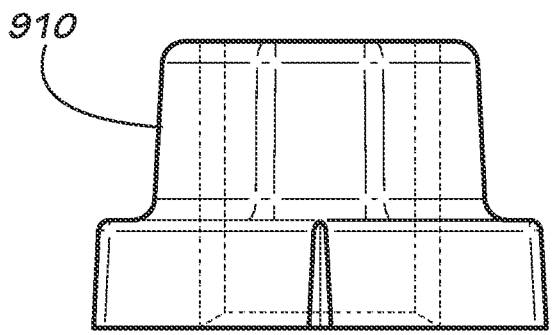
FIG. 9C is a side view of the disc nut of FIG. 9A.
Figure 10A:
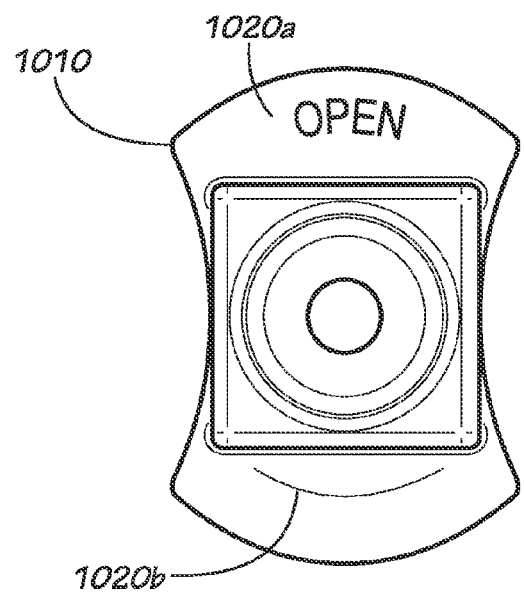
FIG. 10A is a top view of a disc nut for use with the subassembly of FIG. 1 in a gate valve.
Figure 10B:
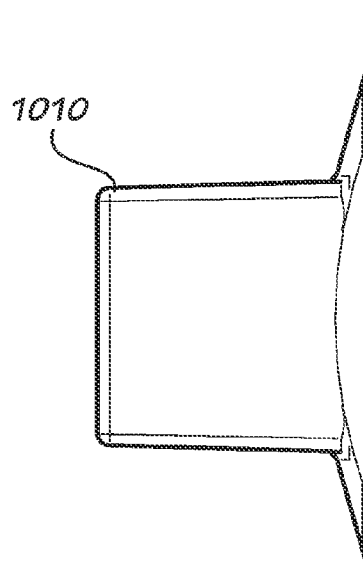
FIG. 10B is a side view of the disc nut of FIG. 10A.
Figure 10C:
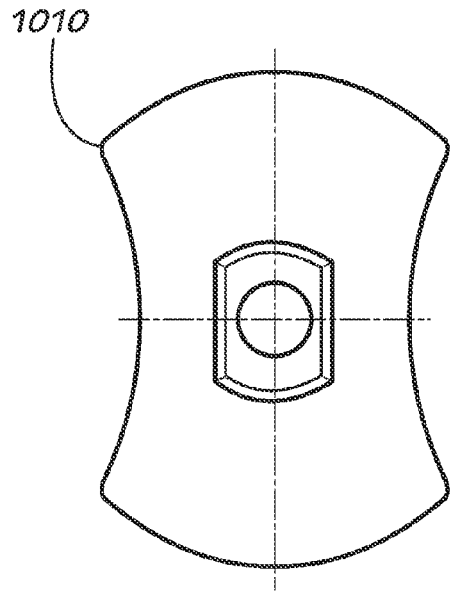
FIG. 10C is a bottom view of the disc nut of FIG. 10A.
Figure 11:
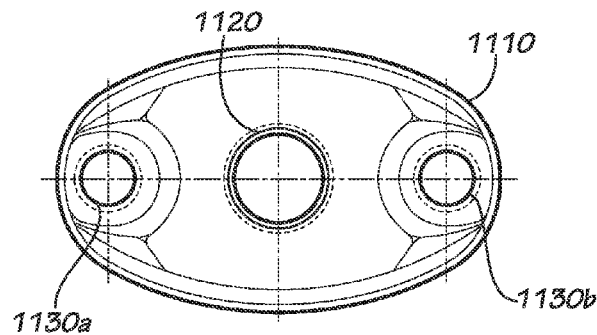
FIG. 11 is a top view of a top cover for use with the subassembly of FIG. 1 in a gate valve.
Figures 12, 12A, 12B:
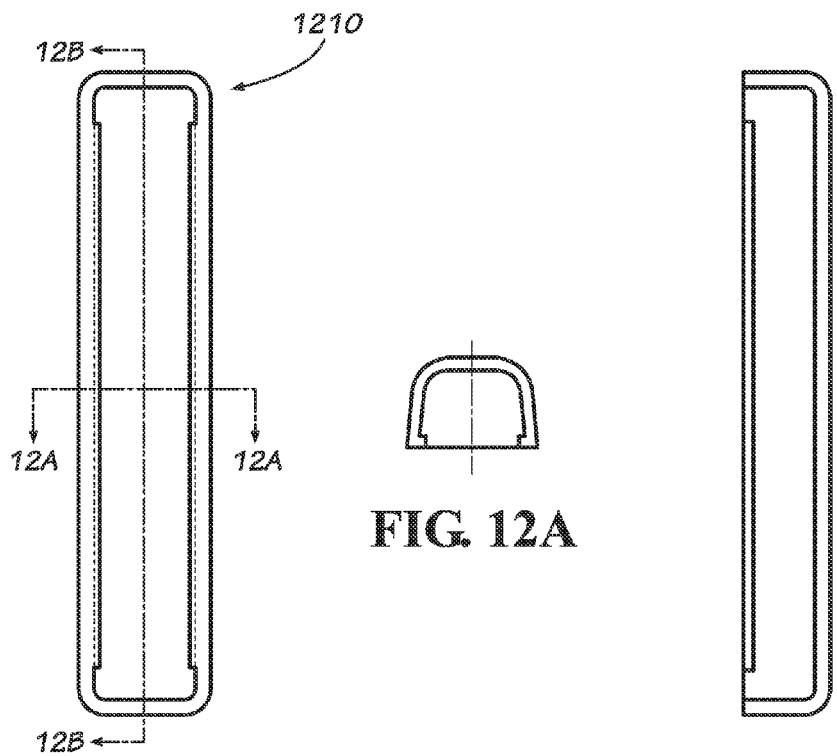
FIG. 12 is a side view of a guide cap for use with the subassembly of FIG. 1 in a gate valve.
FIG. 12A a cross-sectional view of the guide cap taken in a plane indicated by line 12A in FIG. 12.
FIG. 12B a cross-sectional view of the guide cap taken in a plane indicated by line 12B in FIG. 12.

As seen in FIGS. 7A-7C, encapsulated disc 710 can be added to subassembly 100 as part of a gate valve 1000 in accord with one embodiment of the disclosure. As seen the encapsulated disc 710 includes a contact surface 715 for contacting and sealing with the valve seat 215 (seen in FIG. 2). The encapsulated disc 710 is coated in a water-impervious material that aids in sealing the gate valve 1000 when in the closed position. The encapsulated disc 710 includes an actuation bore 725. The encapsulated disc 710 is actuated by a stem 810 which is seen in FIGS. 8A and 8B. The stem 810 includes a threaded portion 815 that interacts with the actuation bore 725. The stem 810 also includes a nut portion 820 that can be rotated by the users to actuate the encapsulated disc 710 and to open or to close the gate valve 1000 selectively. FIGS. 9A-9C show various views of a disc nut 910 that couples the stem 810 and the encapsulated disc 710. FIGS. 10A-10C show various views of a wrench nut 1010 which includes indicators 1020a,b showing the direction of turning to place the gate valve 1000 in an open position. FIG. 11 shows a top cover 1110. The top cover 1110 includes an actuation bore 1120 and two connection bores 1130a,b. FIG. 12 shows a guide cap 1210. The guide cap 1210 is attached to the side of the encapsulated disc 710 to help prevent friction binding of the encapsulated disc 710 against the body 110. The guide cap 1210 is made of plastic in the current embodiment, although other similarly non-binding materials may be used in various embodiments. FIG. 12A shows a cross-sectional view of the guide cap taken in a plane indicated by line 12A in FIG. 12, and FIG. 12B shows a cross-sectional view of the guide cap taken in a plane indicated by line 12B in FIG. 12.

Figure 13A:
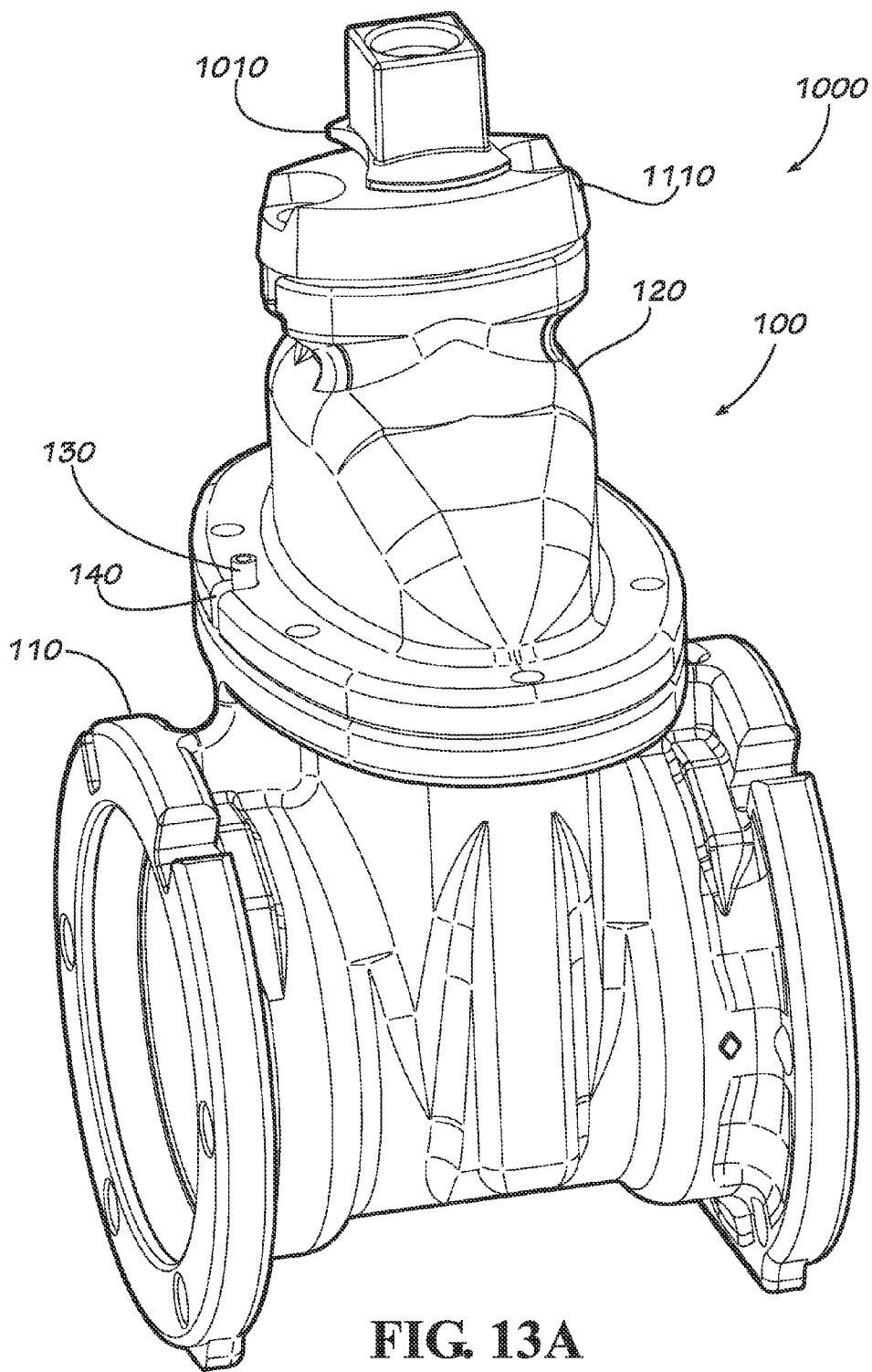
FIG. 13A is a perspective view of a gate valve in accord with one embodiment of the current disclosure including the subassembly of FIG. 1.
Figure 13B:
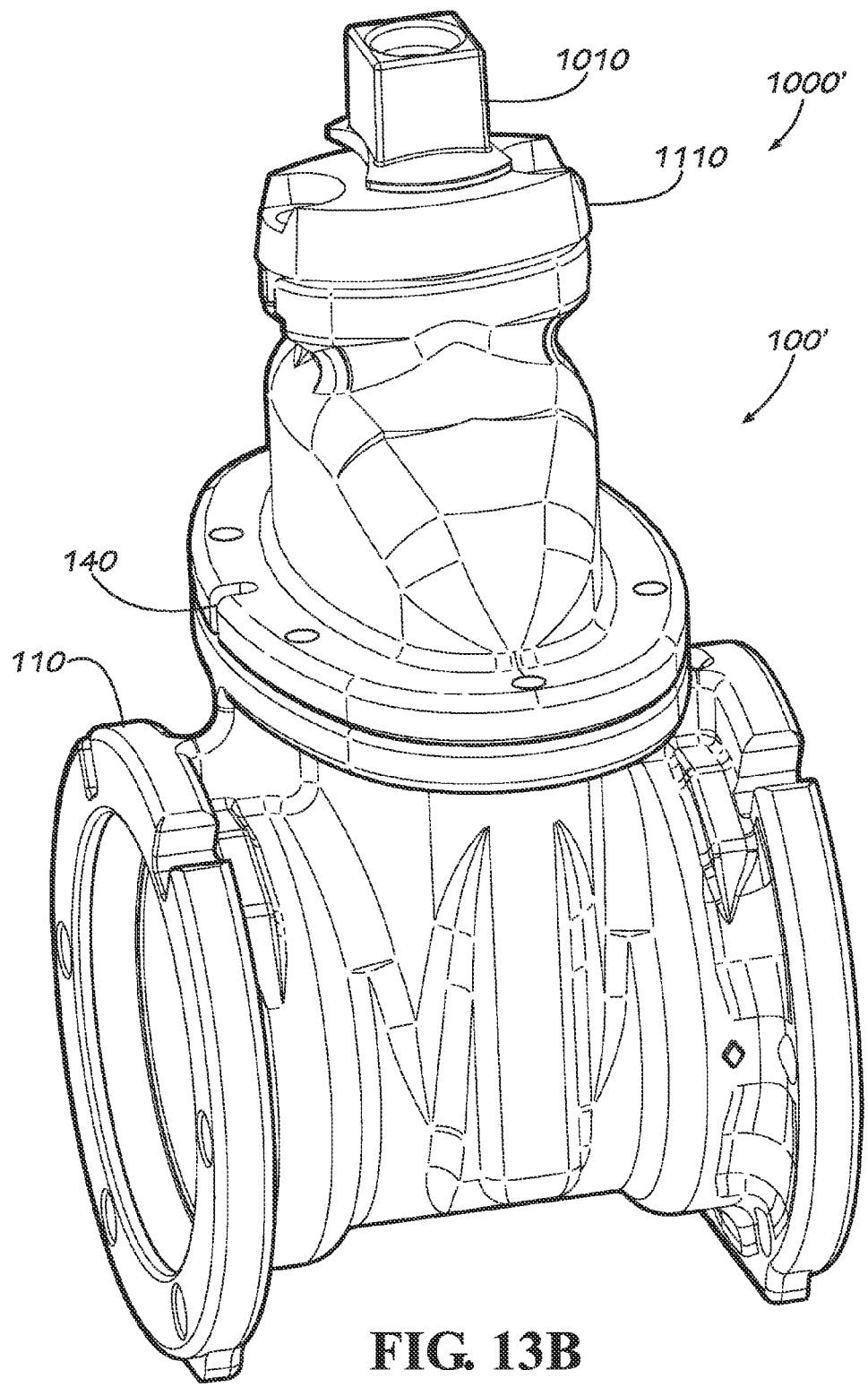
FIG. 13B is a perspective view of a gate valve in accord with one embodiment of the current disclosure including the subassembly of FIG. 4.
Figure 14:
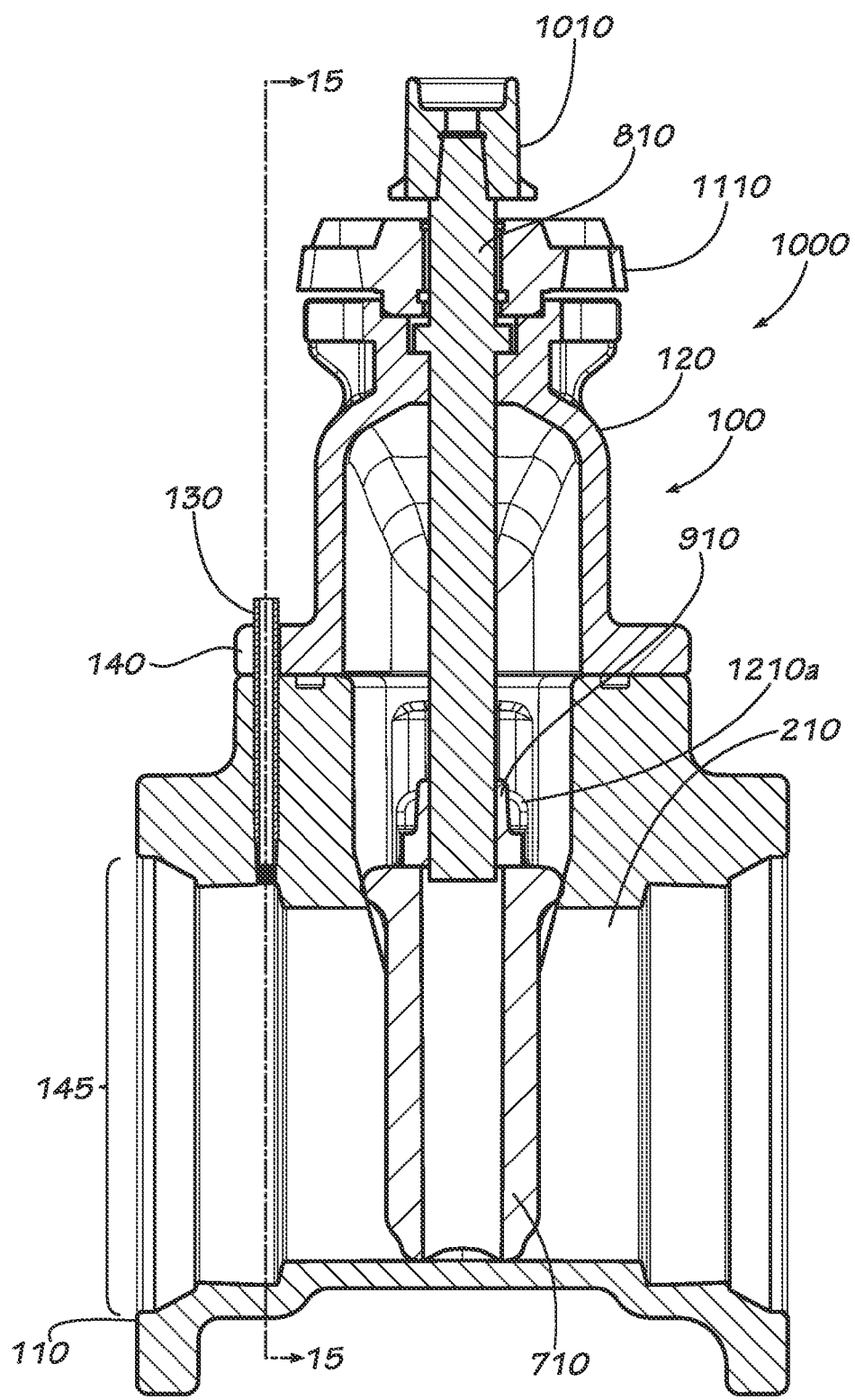
FIG. 14 is a cross-sectional view of the gate valve of FIG. 13A.
Figure 15:
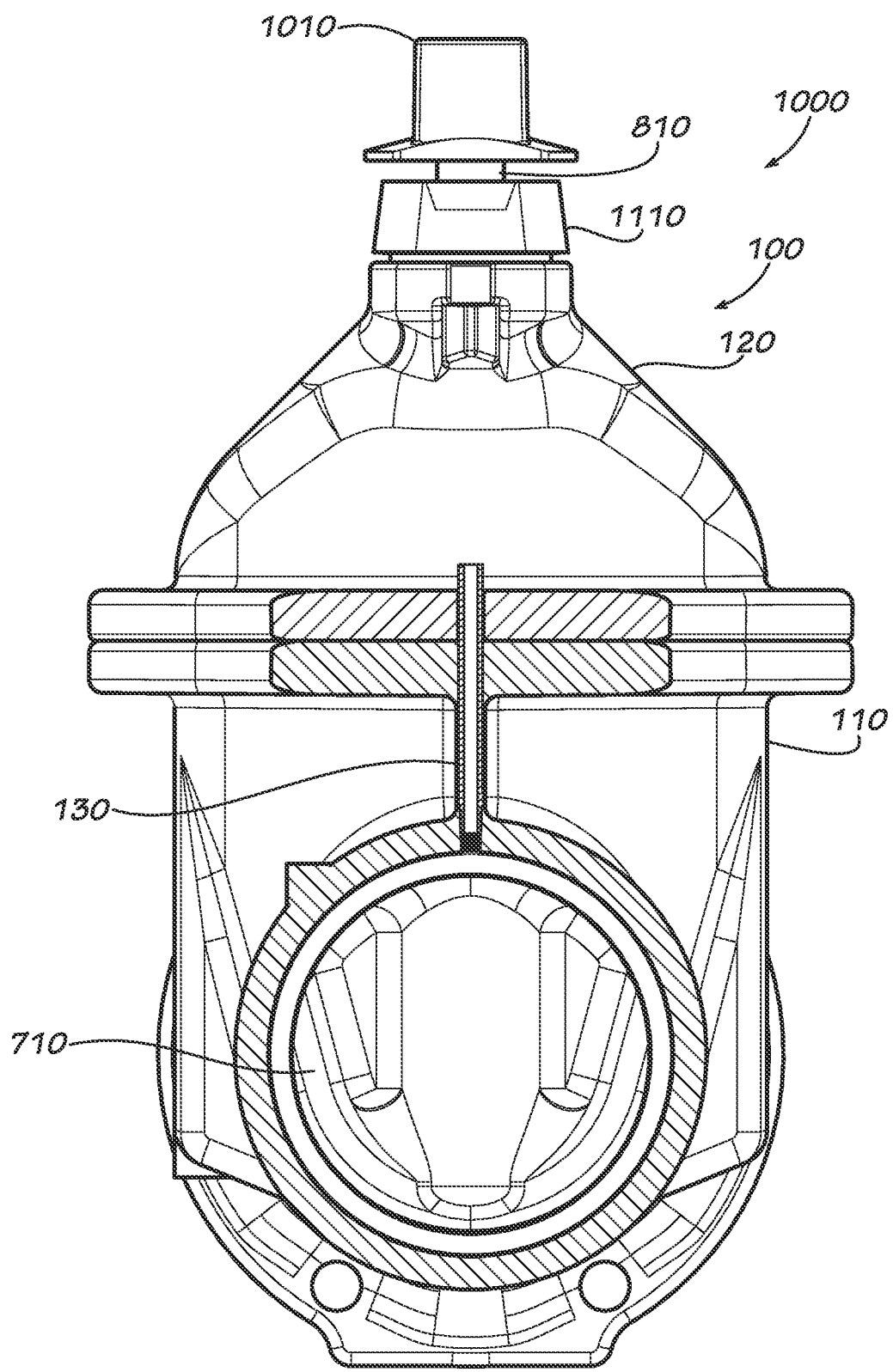
FIG. 15 is a cross-sectional view of the gate valve taken in a plane indicated by line 15 in FIG. 14.
Figure 16:
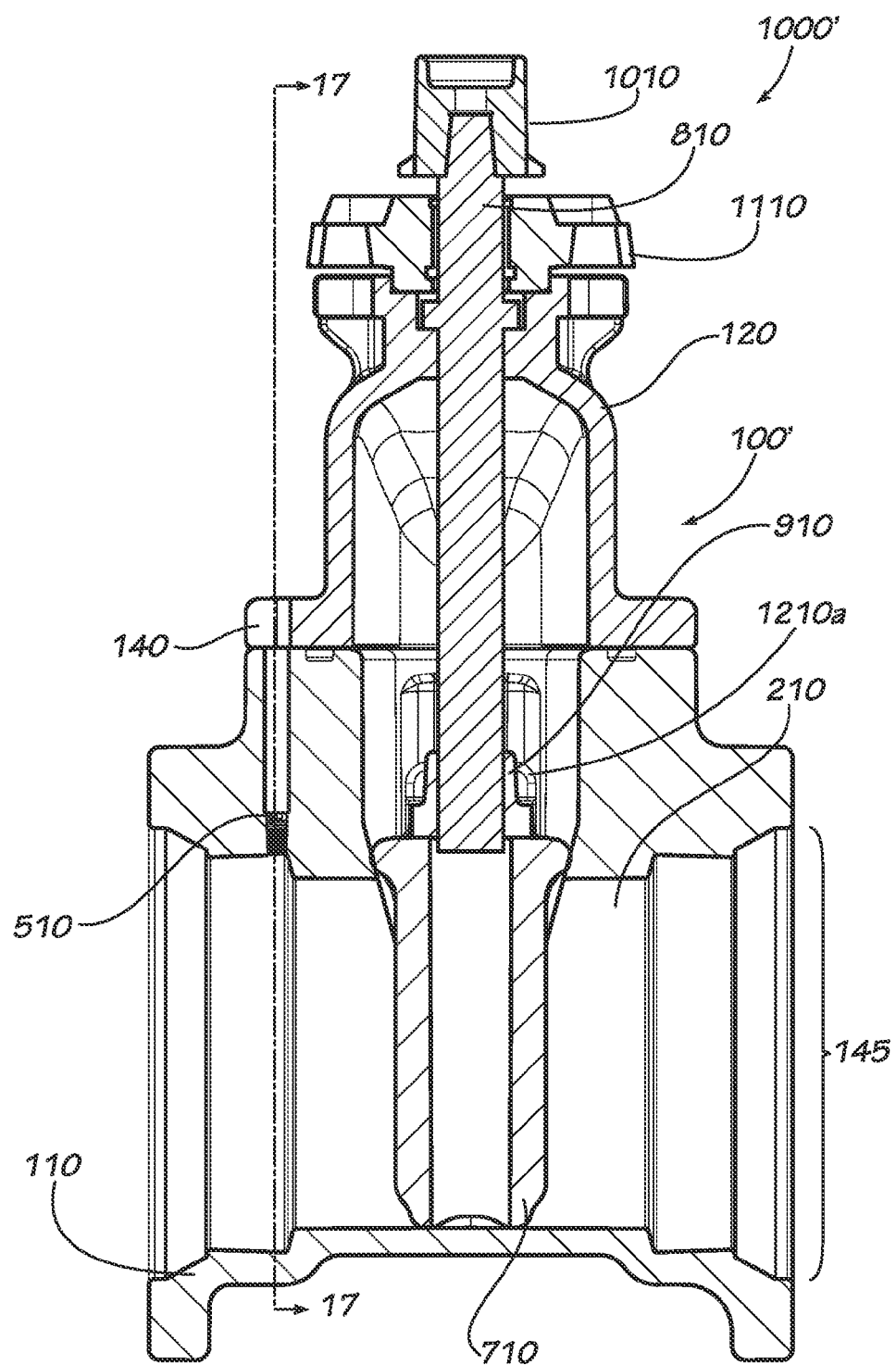
FIG. 16 is a cross-sectional view of the gate valve of FIG. 13B.
Figure 17:
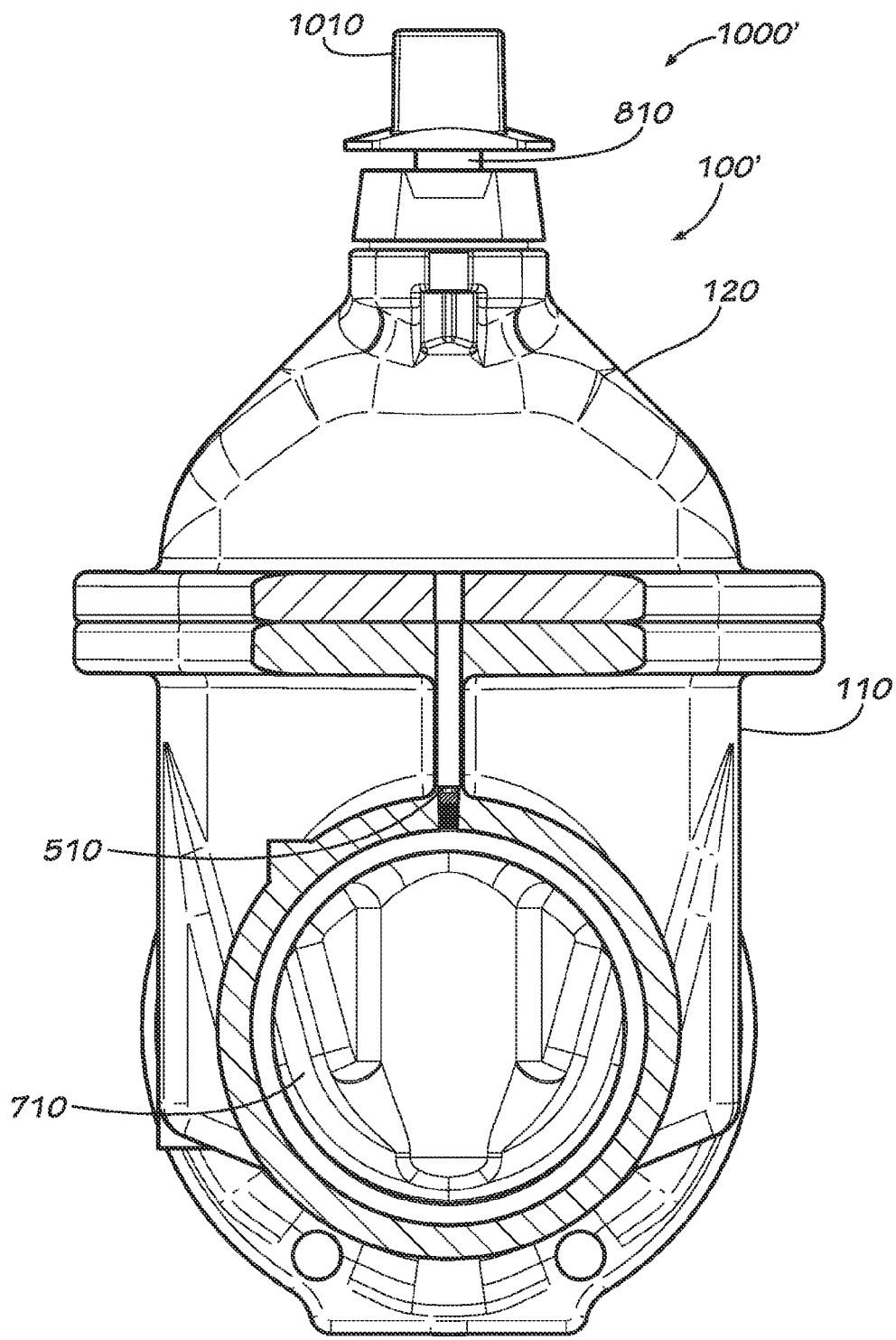
FIG. 17 is a cross-sectional view of the gate valve taken in a plane indicated by line 17 in FIG. 16.

Seen in FIG. 13A, a gate valve 1000 may incorporate the subassembly 100 along with the encapsulated disc 710 (not shown), the stem 810 (not shown), the disc nut 910 (not shown), the wrench nut 1010, the top cover 1110, and guide caps 1210a,b (not shown). As seen in FIG. 13B, a gate valve 1000' may include subassembly 100' as well. FIGS. 14 and 15 show cutaway views of the gate valve 1000. FIGS. 16 and 17 show cutaway views of the gate valve 1000'.

When in use, each gate valve 1000,1000' operates as its main function to allow a user selectively to prevent or to allow water flow through the fluid bore 145. Moving the encapsulated disc 710, the gate valve 1000,1000' can be sealed when the contact surface 715 is seated against the valve seat 215. Actuation of the stem 810 moves the encapsulated disc 710 out of the flow path of fluid, thereby opening the flow.

When the vein 130 is included, as in gate valve 1000, the sensing bore 230 and the bore 350 of the vein 130 provide a fluid pathway in fluid communication with the interior 210 of the body 110. Because fluid in a piping system is under pressure, fluid is forced through the fluid pathway, and pressure equalizes with the pressure inside the gate valve 1000. As such, a pressure sensor may be placed on the shank end 360 of the vein 130 to sense pressure within the piping system.

In other embodiments, other types of sensors may be connected to the vein 130 to sense other aspects of fluid in the system, including (particularly when the fluid is water) turbidity, chlorination, and acidity (pH), among others. In the current embodiment, the vein 130 allows sensors to be placed outside of the gate valve 1000, thereby providing a non-intrusive means of measuring aspects of the fluid in the piping system. However, some sensors may be placed proximate the thread end 370 of the vein 130 or, in some embodiments, may protrude inside the fluid bore 145. In particular, MEMS (microelectromechanical systems) sensors may be especially adapted for the small spaces of the bore 350.

It is common for gate valves such as gate valve 1000 to be buried six feet or more below the surface of the earth. In some embodiments, sensors such as the pressure sensor may be read electronically and may include wires leading to the surface. In some embodiments, the wires may be connected to a remote communicator such as an RF device. In some embodiments, the RF device will correspond with a mesh network. In those embodiments, it may be possible for the mesh network to measure pressure along different points in the piping system, thereby making easier determination of where leaks, blockages, or other failures in the piping systems may occur.

Gate valve 1000' may be provided as a sensor-capable gate valve, such that the vein 130 is not included with the assembly but may be added by the user.

It should be emphasized that the embodiments described herein are merely possible examples of implementations, merely set forth for a clear understanding of the principles of the present disclosure. Many variations and modifications may be made to the described embodiment(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

One should note that conditional language, such as, among others, "can," "could," "might," or "may," unless specifically stated otherwise, or otherwise understood within the context as used, is generally intended to convey that certain embodiments include, while alternative embodiments do not include, certain features, elements and/or steps. Thus, such conditional language is not generally intended to imply that features, elements and/or steps are in any way required for one or more particular embodiments or that one or more particular embodiments necessarily include logic for deciding, with or without user input or prompting, whether these features, elements and/or steps are included or are to be performed in any particular embodiment.

Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

The invention claimed is:

1. A gate valve comprising:
 a body;
 a sensing bore defined in the body;
 a bonnet, and
 a vein, wherein the vein extends through the bonnet and the sensing bore.

2. The gate valve of claim 1, wherein the sensing bore is defined in webbing of the body.

3. The gate valve of claim 1, wherein the sensing bore is defined between the bonnet and an inlet end of the body.

4. The gate valve of claim 1, wherein a notch relief is defined in the bonnet.

5. The gate valve of claim 4, wherein the sensing bore is accessible through the notch relief of the bonnet.

6. The gate valve of claim 1, wherein a diameter of the vein is about equal to a diameter of the sensing bore.

7. The gate valve of claim 6, wherein the sensing bore includes threading and wherein the vein includes threading to mate with the threading of the sensing bore.

8. The gate valve of claim 1, further comprising a plug, the plug including threading to mate with threading of the sensing bore.

9. A subassembly comprising:
 a body, the body defining a sensing bore;
 a bonnet contacting the body; and
 at least one of a vein and a plug in the sensing bore, wherein the vein extends through a notch relief in the bonnet.

10. The subassembly of claim 9, wherein the sensing bore is defined in webbing of the body.

11. The subassembly of claim 9, wherein the body defines a valve cavity, the subassembly further comprising a gate and a stem in the valve cavity, the stem coupled to the gate.

12. The subassembly of claim 9, where the sensing bore includes threading to mate with at least one of the vein and the plug.

13. The subassembly of claim 9, wherein the vein includes an end, wherein a sensor may be mounted to the end.

* * * * *